United States Patent [19]

Leurink et al.

[11] Patent Number: 4,737,214
[45] Date of Patent: Apr. 12, 1988

[54] METHOD FOR PROVIDING STERILE CONNECTION OF PLASTIC TUBES OR THE LIKE

[75] Inventors: Hendrik J. Leurink, Odoorn; Andries C. J. Kuivenhoven, Emmen, both of Netherlands

[73] Assignee: NPBI Nederlands Produktielaboratorium voor Bloedtransfusieapparatuur en Infusievloeistoffen B. V., Emmer-Compascuum, Netherlands

[21] Appl. No.: 882,264

[22] Filed: Jul. 7, 1986

[30] Foreign Application Priority Data

Jul. 5, 1985 [EP] European Pat. Off. ........ 85108384.0

[51] Int. Cl.⁴ ..................... A61M 5/00; B29C 27/00
[52] U.S. Cl. ................................. 156/158; 156/304.2; 604/905
[58] Field of Search .............. 156/158, 159, 304.2, 156/304.5, 304.6; 604/905, 280

[56] References Cited

U.S. PATENT DOCUMENTS 3,968,195 7/1976 Bishop .............................. 156/304.2
4,619,642 10/1986 Spencer ............................. 604/905

Primary Examiner—Michael Ball
Attorney, Agent, or Firm—Karl F. Ross; Herbert Dubno

[57] ABSTRACT

A process and apparatus for sterile docking of plastic tubes or the like is disclosed in which the tube ends to be joined are sealed by a transverse weld seam and aligned along a common axis. A heating unit is moved between the tube ends at a distance thereto to melt the latter. After retracting the heating unit, the tube ends are urged together. Prior to and during the heating, the tube ends are squeezed behind the weld seam. Immediately after contacting together the tube ends, the squeezing action is discontinued to provide a sterile docking and an opening of the sealed ends.

3 Claims, 2 Drawing Sheets

METHOD FOR PROVIDING STERILE CONNECTION OF PLASTIC TUBES OR THE LIKE

FIELD OF THE INVENTION

Our present invention relates to a method of and to an apparatus for the sterile connection of plastic tubes (synthetic resin) or the like. More particularly, the invention is concerned with the sterile docking of plastic tubes which especially are affixed to plastic bags for circulating human blood, infusions etc. and which may also be used as bags for e.g. receiving human blood, infusions etc.

BACKGROUND OF THE INVENTION

The tubes are usually sealed at their respective ends to be joined by a squeeze weld seam extending transversely to the tube axis. The tube ends are inserted in aligned position along a common axis in two mounting blocks which are movable relative to each other. By means of a heating unit movable between the mounting blocks, the facing ends are melted. After removing the heating unit, the tube ends are pressed against each other in axial direction.

From the European patent No. EP-A2 No. 00 44 204, such an apparatus and process is known. The plastic tubes are inserted in overlapping manner in the respective mounting blocks. The heating unit is of the electrically heated blade type which is moved between the mounting blocks and cuts off both exposed overlapping tube sections with their respective weld seam while sealing the molten interface between the facing tube ends. The fusing contact is maintained even after subsequent relative movement of the mounting blocks which align the tube ends to be joined along a common axis.

Several drawbacks are encountered with this apparatus and method. Since each docking and splicing operation requires a preceding cutting of certain tube sections, considerable amount of waste accumulates which is undesirable from an economical standpoint, and which severely limits the number of possible joining processes depending on the length of the tube. In view of the unavoidable relative movements between the fused interfaces and the heated blade in the joining area, plastic beads are encountered which will increase the flow resistance. Further, the sealing of the tube ends may be disrupted during retraction of the heating unit so that contamination can penetrate into the tube. To maintain sterility of the process, it is necessary to exchange the blades prior to each docking because residues of plastic material stick to the heated blades.

Apart from these drawbacks, the apparatus according to No. EP-A2 No. 00 44 204 requires also complicated guiding means as the mounting blocks are not only moved in transverse direction relative to the heating unit and relative to each other in longitudinal direction but also in transverse direction relative to each other.

U.S. Pat. No. 3,968,195 discloses a method for making sterile connections between two tubelike blood bags. Before docking, the tube is closed off by clamps at a distance from the free ends of the aligned tubes. A Bunsen burner is used to apply heat to the free tube ends which are softened and then brought into contact. After holding the tube end in this position and allowing them to cool and to solidify, a permanent connection is formed.

This has the disadvantage, however, that the tube end sections must be designed in a special and complicated manner. As disclosed therein, in the tube end, a rigid tube is inserted whose free end is sealed off by a thin thermoplastic diaphragm.

OBJECT OF THE INVENTION

It is thus the principal object of our present invention to provide an improved method of and apparatus for the sterile joining of plastic tubes or the like obviating the afore-stated drawbacks.

Another object is to provide a simple and economical coupling of two thermoplastic tubes.

SUMMARY OF THE INVENTION

We realize this object, in accordance with the present invention, by aligning the plastic tubes with their ends sealed by a weld seam at a distance from an interposed heating unit such that the weld seams of the sealed tube ends extend parallel to each other, and squeezing the tubes behind the sealed tube ends perpendicular to the latter. Once melting of the tube ends has occurred and the heating unit is removed, the aligned tube ends are axially contacted together wherein shortly thereafter the squeezing of the tube ends is discontinued.

According to the invention, the tube ends are aligned by a pair of two-part mounting blocks which are provided with a slot to receive the tube ends. The slot of each block extends in moving direction along a major portion of the entire width of the respective block part so that a transverse rib is defined which after inserting the tube ends and closing the blocks squeezes the tube behind the weld seam.

The invention is based upon our surprising discovery that plastic tubes sealed by weld seams can be directly connected without any waste and without contacting the tube ends to be joined by squeezing the tube ends perpendicular to the weld seams. Through this measure, the automatic self-opening of the weld seams is avoided until the axial contacting together of the tube ends. Thereafter, i.e. after discontinuing the squeezing action, this automatic self-opening effect is utilized to open the tube channel. An advantage of this method according to the invention is the prevention of any internal beads. There is no necessity to cut off tube sections, and moreover, the contactless melting of the tube ends renders the apparatus very simple and most economical but still guaranteeing the sterility of the connection.

BRIEF DESCRIPTION OF THE DRAWING

The above and other objects, features and advantages of our present invention will now become more readily apparent from the following description, reference being made to the accompanying drawing in which.

SPECIFIC DESCRIPTION

Figure 1:
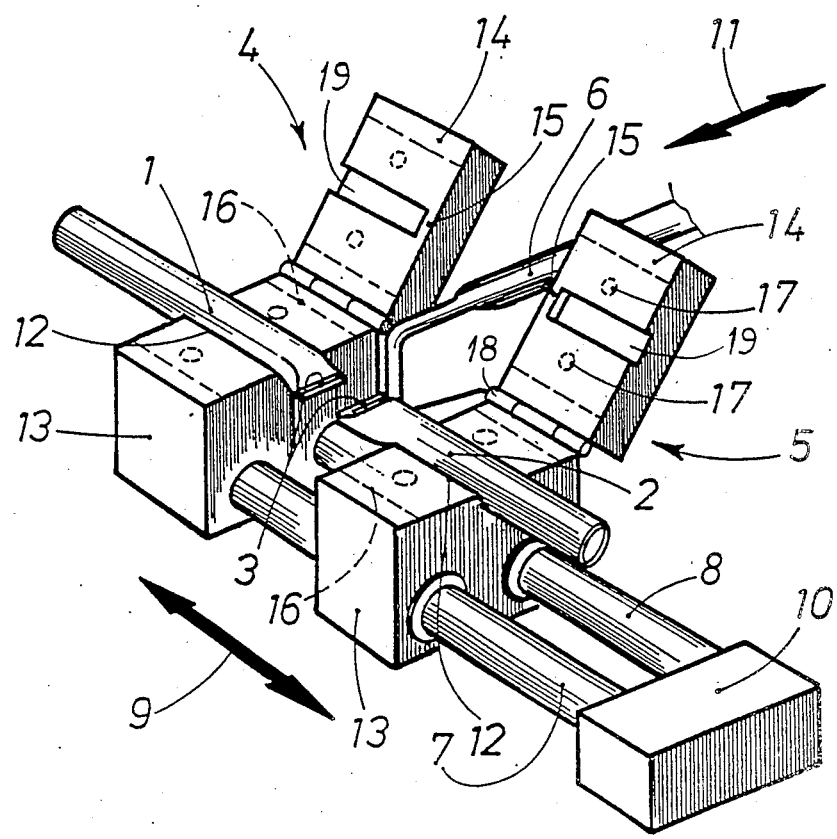
FIG. 1 is a perspective illustration of one embodiment of a joining apparatus according to the invention.

In FIG. 1, one embodiment of an apparatus for sterile joining or docking of plastic tubes 1,2 is shown in perspective view. The plastic tubes 1,2 are connected for example with blood bags and sealed at their one end by a weld seam 3 extending transversely to the tube axis.

The apparatus according to one embodiment of the invention includes a stationary mounting block generally designated by reference numeral 4 cooperating with a movable mounting block generally designated by reference numeral 5. The mounting block 4 is provided with a pair of spaced guide rods extending parallel to each other and traversing through suitable throughholes of the mounting block 5 so that the latter is accurately movable by suitable means (not shown) towards and away from the mounting block 4 along the guide rods 7,8 as indicated by double arrow 9. The other end of the guide rods 7,8 remote to the mounting block 4 is connected by a stop block 10 which thus limits the movement of the mounting block 5 along the rods 7,8.

Each block 4,5 is a two-part element 13,14 hinged to each other at 18 so as to allow opening and closing of the blocks. Block part 13 of each mounting block 4,5 is provided with a continuous semicircular slot 12 extending parallel to the guide rods 7,8 and serving as receptacle for the tubes 1,2, respectively. The other part 14 which in FIG.1 is shown in its open position is provided with a rectangular groove 19 cooperating with the slot 12 and extending along the width of the block part 14 short of the edge in vicinity of the tube ends to define a web or rib 15 whose purpose will be described hereinbelow.

As is shown in FIG. 1, the slots 12 of the parts 13 are aligned to receive the straight ends of tubes 1,2. Likewise, the grooves 19 of the parts 14 are aligned.

Cooperating with the mounting blocks 7,8 is a heating unit 6 which includes an electrically heated plate movable in direction of double arrow 11 perpendicularly between the mounting blocks 7,8.

Although not explicitly shown in the drawing, the facing tube ends to be joined can be provided with flanges so as to be held accurately during the docking step. Moreover, as indicated schematically by broken lines, the mounting blocks 4,5 may be provided with recesses 16 engageable by respective pins 17 to enhance the positioning of the parts 13,14 of each mounting block 4,5. Depending on the dimensioning of the tube ends to be connected, it is conceivable that the opening effect of the tube ends after docking is not sufficient in view of the tube elasticity so that the tube channel may not be continuous. Thus, pressure fingers (not shown) are arranged which are insertable between the mounting blocks 4,5 for securing the opening of the joined tube ends. Certainly, this opening may also be obtained manually by pressing the tube ends after the docking step.

Figure 2:
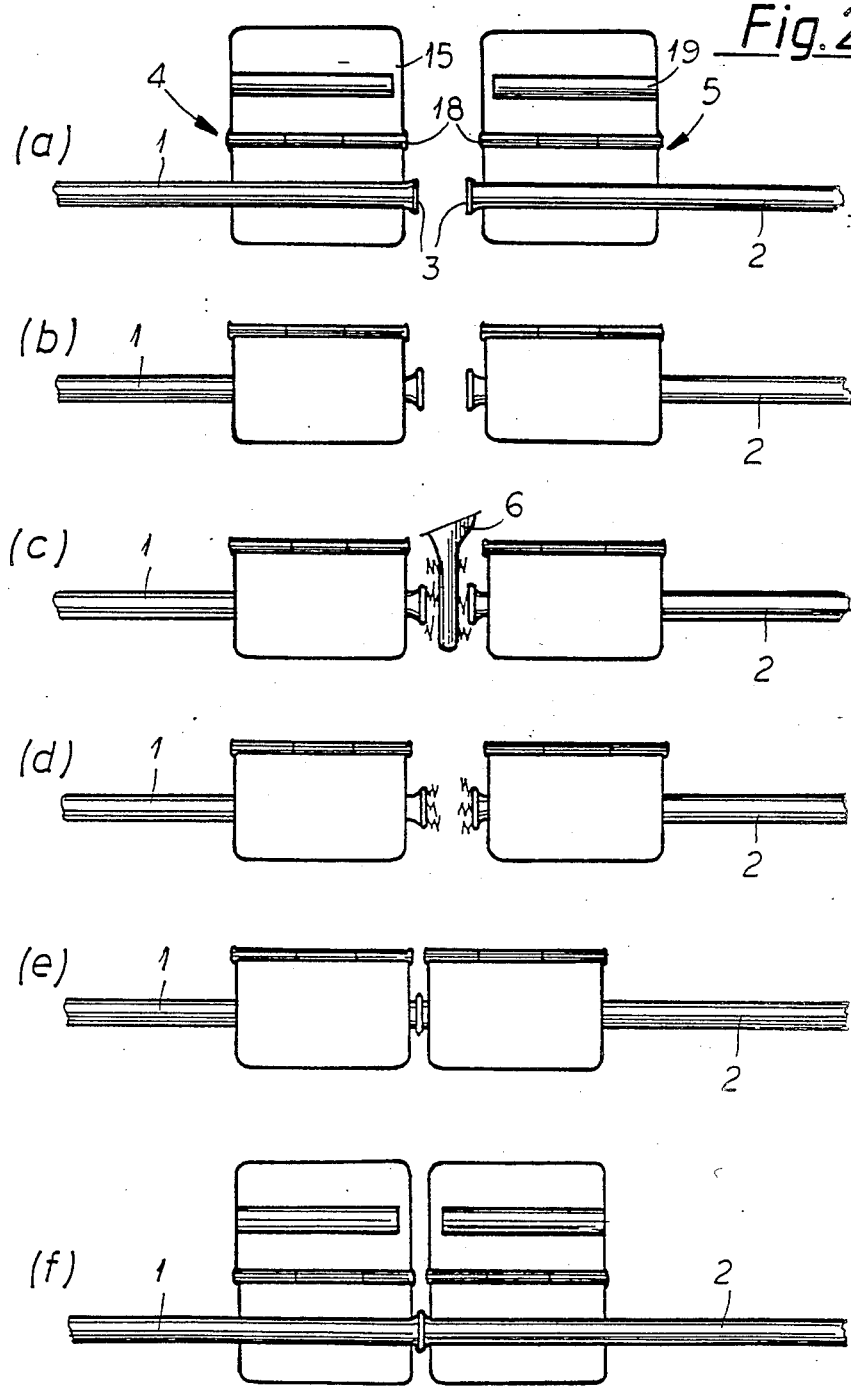
FIGS. 2a–2F are simplified illustrations of FIG. 1 showing successive steps of a joining process in accordance with the present invention.

For coupling two tubes or tube sections 1,2 made of plastic material, e.g. thermoplastic, the respective tube ends with their weld seams 3 facing each other at a distance and extending parallel to each other are inserted into the aligned slots 12 of the mounting blocks 4,5 such that the tube ends are arranged along one common axis with the forward end of each tube 1,2 extending beyond the blocks 4,5 (FIG. 2a).

Thereafter, the mounting blocks 4,5 are closed by pivoting the block part 14 onto the part 13 (FIG. 2b).

Upon closing the mounting blocks 4,5, the ribs 15 squeeze the tube ends behind the seam 3 perpendicular thereto.

The seams 3 of the tube ends and thus the mounting blocks 4,5 are sufficiently spaced from each other to allow the heating unit 6 to move centrally therebetween without touching or contacting the tube ends (FIG. 2c). Consequently, melting of the tube ends is provided solely by heat radiation and heat convection.

After melting, the heating unit 6 is retracted leaving the tube ends in a molten state (FIG. 2d) and the tube ends are pressed against each other by sliding the mounting block 5 towards the mounting block 4 (FIG. 2e).

Immediately thereafter, i.e. at a moment at which the end faces of the tubes adhere to each other but the molten plastic material has not yet solidified, the mounting blocks 4,5 are opened again to allow the weld seams 3 to automatically open up due to the tube elasticity. As already mentioned, the opening of the seam 3 can be supported by pressing the tube with, e.g. two fingers.

SPECIFIC EXAMPLE

With the following example, the sterility of the joined tube ends is demonstrated.

Two gamma-sterilized PVC-tubes are contaminated around seam 3 several times with microflora of human hands and with spores of bacillus stearothermophillus from a dissolution of a concentration of $4 \times 10^8$ spores/ml. After docking, the tubes are flushed with growth medium TSB which was controlled for growth after an incubation period of 7 days. In neither case could a bacterial growth be detected.

We claim:

1. A method of sterile docking of plastic tubes or the like, comprising the steps of: aligning the plastic tubes with their ends sealed by a weld seam in axial direction such that the weld seams of the sealed tube ends extend parallel at a distance to each other;
    squeezing the tubes behind the sealed tube ends perpendicular to the latter;
    heating the sealed tube ends by interposing a heating unit therebetween at a distance to the tube ends;
    removing the heating unit;
    contacting together the aligned heated tube ends in axial direction; and
    discontinuing the squeezing of the tube ends immediately after the contacting step.

2. The method defined in claim 1, further comprising the step of providing the tube ends with guide flanges for maintaining the tube ends in position.

3. The method defined in claim 1, further comprising the step of pressing open the contacted tube ends towards the weld seams immediately after said discontinuing step.

* * * * *